(12) United States Patent
Stiller et al.

(10) Patent No.: US 6,699,239 B1
(45) Date of Patent: Mar. 2, 2004

(54) LASER INSTRUMENT

(75) Inventors: Hans-Peter Stiller, Bavaria (DE); Robert Ibler, Bavaria (DE); Thomas Hurland, Bavaria (DE)

(73) Assignee: Dornier Medtech Systems GmbH, Wessling (DE)

( * ) Notice: Subject to any disclaimer, the term of this patent is extended or adjusted under 35 U.S.C. 154(b) by 0 days.

(21) Appl. No.: 09/700,948
(22) PCT Filed: May 18, 1999
(86) PCT No.: PCT/DE99/01507
§ 371 (c)(1), (2), (4) Date: Feb. 28, 2002
(87) PCT Pub. No.: WO99/59483
PCT Pub. Date: Nov. 25, 1999

(30) Foreign Application Priority Data

May 18, 1998 (DE) .......................................... 198 21 986

(51) Int. Cl.$^7$ ............................................... A61B 18/22
(52) U.S. Cl. ........................................... 606/15; 606/13
(58) Field of Search ..................................... 606/13–18

(56) References Cited

U.S. PATENT DOCUMENTS 5,416,878 A  5/1995  Bruce
5,693,043 A  12/1997 Kittrel et al.

FOREIGN PATENT DOCUMENTS

EP  0 325 836 A   8/1989
EP  0 404 968 A   1/1991
EP  0 514 258 A1  11/1992
EP  0 433 464 B1  6/1995

Primary Examiner—Lee Cohen
Assistant Examiner—Henry M. Johnson, III
(74) Attorney, Agent, or Firm—King & Spalding LLP

(57) ABSTRACT

A laser instrument that can perform effective vaporization of biological tissue and stabilization of the application cap during tissue removal is provided. The laser instrument includes an optical waveguide with a light guide portion that emits light and an application cap coupled to the optical waveguide that transmits light. The laser instrument can be inserted into an endoscope and extended or retracted to position the application cap for vaporization and removal of biological tissue.

10 Claims, 1 Drawing Sheet

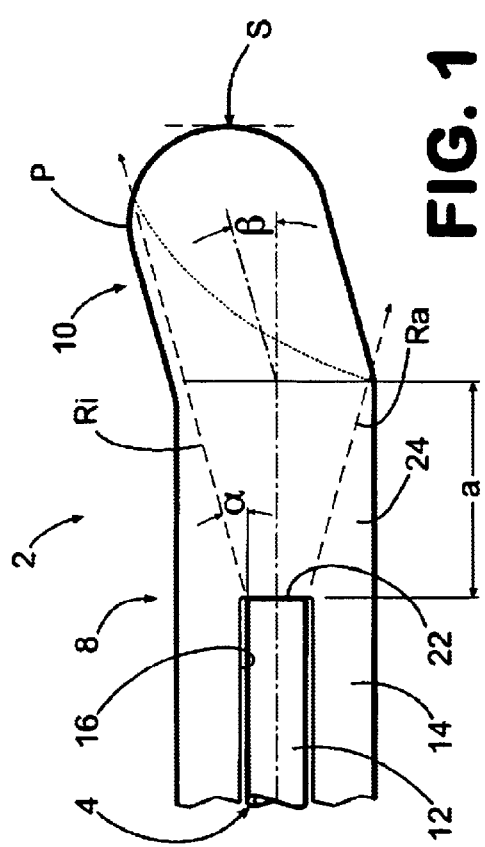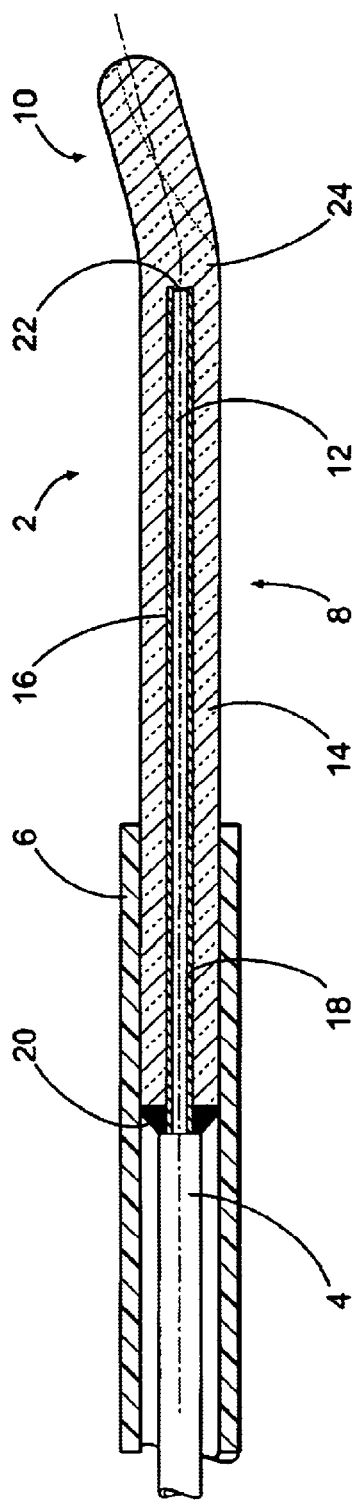

LASER INSTRUMENT

TECHNICAL FIELD

The invention pertains to a laser instrument for use in non-invasive or minimally invasive operations for the vaporization of biological tissue.

BACKGROUND OF THE INVENTION

Laser instruments are used in combination with an endoscope for non-invasive or minimally invasive operations for the vaporization by contact of biological tissue, primarily in narrow-lumen hollow organs, for example, for transurethral tissue resection of the prostate in cases of benign prostatic hyperplasia. With one such laser instrument, known from EP 0 514 258 A1, the application cap fastened on the distal end of the laser light guide is bent, along with the light guide end, so that the laser irradiation emerges from the application tip in the form of a ray which is slanted at an angle to the axis of the instrument. In this regard, a danger exists that the application cap will drift in an uncontrolled fashion in the direction of the application tip during the treatment, i.e., laterally to the direction of movement, so that a target-precise, patient-friendly removal of tissue is made extremely difficult or even impossible within a closely surrounded treatment area.

Further, known from EP 0 433 464 B1 is a laser surgery applicator with a bent application tip which is topically coated with radiation-absorbing and light-scattering particles in order to obtain different treatment effects in individual surface sections of the applicator. Specifically, a more coagulating radiation treatment effect and a more cutting radiation treatment effect are obtained. The upward-bent application tip is illuminated on the surface areas on the outside of the bend primarily by diffuse light, so that a weak vaporization effect results there, and this applicator can thus be used for effective tissue ablation only to a very limited extent.

The objective of the invention is to provide a laser instrument similar to the types cited above that can perform effective biological tissue vaporization in both the prograde and the lateral directions relative to the instrument axis, and at the same time, can perform stabilization of the application cap during the tissue removal.

SUMMARY OF THE INVENTION

According to the invention, the above objective is achieved with a laser instrument that includes a special geometric configuration of the application cap. With this special geometric configuration of the application cap, the exit surface of the laser light bundle becomes significant. Namely, the laser light bundle becomes widened outward over the entire surface region o of the outer part of the bend at least as far as the outermost distal tip, but not over the radially outermost surface point of the bent part. As a result, with only a slight enlargement of the external dimensions of the application cap, an extremely effective vaporization of tissue is achieved. More specifically effective vaporization of tissue is achieved not just laterally, but also in the direction of the instrument axis, so that in addition to a long removal of tissue, a rechannelization of stenosed hollow organs is easily possible as well. Furthermore, the part of the bent applicator surface on the inner part of the bend is masked from the ray path of the laser light bundle. As a result of the distribution of vaporization and non-irradiated applicator sub-surfaces that is achieved, in combination with the sliding effect on the bent part, an automatic stabilization of the applicator cap is assured, and the danger of an uncontrolled vaporization of tissue or a adhering of tissue to the applicator tip is largely eliminated.

An especially advantageous aspect of the invention provides that at least the region of the bent part from which the ray emerges is roughened. As a result, when the laser instrument according to the invention is moved, small parts of the tissue to be vaporized are mechanically abraded and remain adhered to the roughened surface of the bent part. Under the effects of the laser irradiation, these tissue parts begin to carbonize, and the absorbed laser irradiation generates directly on the surface of the bent part a temperature which allows the tissue material coming into contact with the bent part to be vaporized rapidly.

Another advantageous aspect of the invention; is that the axial cap part is configured on the proximal end as the fiber core of the light guide with a receiving sleeve at a radial distance. This provides the advantage that the light guide is accommodated in a protected position within the applicator cap, while at the same time, a sure guiding of the laser light through the light guide to the distal end of the light guide is retained. In addition to that advantage, the light guide is preferably bonded to the proximal end of the receiving sleeve, and the receiving is designed as a thermal insulation zone according to the length of the sleeve. As a result, a high-strength mechanical coupling between the light guide and application cap is achieved. Furthermore individual heat-sensitive parts, such as the bonding location on the proximal end of the applicator, are effectively protected against overheating.

According to another aspect of the invention, the laser instrument is preferably used in conjunction with an endoscope, and the application cap is the guided in a sliding fashion within the working channel of the endoscope, so that pressure can be exerted on the tissue from the proximal end of the light guide and target-precise handling is made possible. In regard to this aspect of the invention, the length of the receiving sleeve is expediently dimensioned, not just from the standpoint of the thermal insulation zone, but also in such a way that the application cap is guided by means of the receiving sleeve over its entire motion path within the endoscope.

In terms of a high-quality optical coupling of the light guide and the application cap, the distal end of the light guide is expediently fused with the axial cap part. Furthermore, in order to minimize reflections on the light guide-applicator interface, the application cap and the fiber core of the light guide are expediently made of materials with the identical index of refraction and specifically for reasons of a high thermal loading capacity, preferably from quartz glass. For production reasons, the bent part is not continuously curved, but instead expediently runs at an angle to the axial cap part, and preferably, at a bending angle of between 5° and 30°.

Because of its accurately controllable, patient-friendly vaporization effect, the laser instrument according to the invention can be used in many ways, but is used in an especially preferred way for transurethral prostate treatment, particularly in the case of benign prostatic hyperplasia.

BRIEF DESCRIPTION OF THE DRAWINGS

The invention will now be explained in more detail through the use of exemplary embodiments in combination with the drawings. Shown in schematic form are the following:

FIG. 1 is a partially sectioned side view of a laser instrument according to the invention in the region of the distal end of the applicators.

FIG. 2 is a complete section view of the applicator and the light guide in conjunction with the distal end of the working channel of an endoscope.

DETAILED DESCRIPTION OF EXEMPLARY EMBODIMENTS

The laser instrument shown in the Figures contains as its main parts an application cap 2 and an optical waveguide 4, which per FIG. 2 can be accommodated in the working channel 6 of an endoscope (not shown). The proximal connection of the optical waveguide 4 to a laser light source, like the remaining parts of the endoscope, including the rinsing agent channels and the visual control function, is of conventional design and therefore not shown in the Figures in detail.

The application cap 2 consists of a cylindrical cap part 8 which is coaxial with the optical waveguide 4, and a bent part 10 which is at an angle to the waveguide 4. The bent part 10 is also cylindrical, but it is rounded at the distal end and is made of the same material as the fiber core 12 of the optical waveguide 4, namely, quartz glass with the same or nearly the same index of refraction. At the proximal end, the axial cap part 8 forms a receiving sleeve 14 for the optical waveguide 4, whereby the lumen 16 of the receiving sleeve 14 has essentially the same diameter as the sheathing 18 of the optical waveguide 4. By means of a bonding 20 between the sheathing 18 and the receiving sleeve 14, the optical waveguide 4 is joined to the application cap 2 in a mechanically fixed and sealed manners. However, the sheathing 18 immediately beyond the bonding location 20 is removed exposing an annular gap between a portion of the wave guide 4 and the receiving sleeve 14, so that only the "light guide" portion of the optical waveguide 4 (for example, the fiber core 12 and possibly the fiber cladding, not shown), runs to the distal end of the receiving sleeve 14. The light guide end 22 is fused to provide a high-quality, low-reflection laser light coupling with the cap part 8.

As shown in FIG. 1, the axial cap part 8 extends beyond the surface of the distal light guide end 22. The length _"a"_ of the extended cap section 24 is dimensioned, in dependency on the angle of divergence _"α"_ of the ray bundle (i.e., the ray path of the laser light bundle) inside the cap part 8, in such a way that the outer bend marginal ray _"Ra"_ of the ray bundle emerges at a maximum exterior angle in the transition region between the axial cap part 8 and the bent part 10. By contrast, the inner bend marginal ray _"Ri"_ of the ray bundle inside the cap 2 remains within cap part 8 and bent part 10 which form a minimum exterior angle on this side, and emerges only at the rounded end of the bent part 10 between the outermost distal tip S and the radially outermost surface point P of the bent part 10. In this regard, the bending angle _"β"_ of the bent part 10 is equal to or greater than the angle of divergence α. However, the bending angle β is also small enough, taking into account the length of the bent part 10, that the entire bend surface area (shaded in FIG. 1) of bent part 10, including the distal application tip S but not the radially inner surface point P, are illuminated from the therapy light (i.e., the laser light), and the remaining surface areas of the cap part 8 and the bent part 10 are masked from the ray path of the laser light bundle.

The application cap 2 is guided within the working channel 6 of the endoscope by the axial part 8, whereby the entire length of the receiving sleeve 14 and the cap section 24 corresponds to the maximum motion path of the application cap 2. As a result, pressure can be exerted on the tissue from the proximal end of the optical waveguide 4 via the application cap 2 without the optical waveguide 4 being pressed, unsupported, out of the distal end of the working channel 6. In addition to the guiding function, the receiving sleeve 14 also takes on the task of thermal insulation, through which temperature sensitive parts, i.e., the bonding 20 in the case of the embodiment shown, are protected from the excessive effects of heat coming from bending part 10, which heats up considerably during the vaporization of tissue.

A typical embodiment of the invention has the following dimensional features. The application cap 2 possesses a total length of 25 mm, the receiving sleeve 14 has a length of 18 mm, the cap section 24 is 2 to 4 mm in length, and the bent part 10 is between 3 and 5 mm long. The outside diameter of the cap 2 is about 1.6 mm and the distance of the radially outermost surface point P from the centerline of the cap part 8 is 1.5 mm. The angle of divergence α of the therapy light within the cap material typically has a value between 3° and 10°, and the bent part 10 is bent at an angle β of 10° to 20° relative to the cap part 8.

What is claimed is:

1. A laser instrument, comprising:
   an optical waveguide comprising a light guide portion having a distal end and configured to emit a light; and
   an application cap coupled to the optical waveguide and configured to transmit the light, comprising:
      an axial cap part, into which the light guide is at least partially inserted, that has a first longitudinal axis; and
      a bent cap part that angularly extends from the axial cap part and has a second longitudinal axis that extends at a first angle relative to the first longitudinal axis, wherein the transition from an exterior surface of the axial cap part to an exterior surface of the bent cap part defines a maximum exterior angle and a minimum exterior angle,
   wherein the axial cap part extends beyond the distal end of the light guide portion for a distance that causes the light emitted from the distal end to be transmitted through the application cap within a first radial limit defined by a first linear path from the distal end through the vertex of the maximum exterior angle, and the first angle has an angular size that causes the light emitted from the distal end to be transmitted through the application cap within a second radial limit defined by a second linear path from the distal end through a distal edge of the exterior surface of the bent cap part that defines the minimum exterior angle.

2. The laser instrument of claim 1, wherein the light transmitted through the application cap within the first radial limit and the second radial limit defines a first transmission surface of the application cap and the exterior of the first transmission surface has a roughened texture that abrades and collects biological tissue that is contacted by the first transmission surface.

3. The laser instrument of claim 1, wherein the axial cap part includes a receiving sleeve section that surrounds the light guide portion of the optical waveguide and extends from a proximal end of the application cap to the distal end of the light guide.

4. The laser instrument of claim 3, wherein the optical waveguide is bonded to the receiving sleeve section at the proximal end of the application cap, and the receiving sleeve has a length that causes the proximal end of the application cap to be thermally insulated from a distal end of the application cap.

5. The laser instrument of claim 1, wherein the distal end of the light guide is fused to the axial cap part.

6. The laser instrument of claim 1, wherein the application cap and the light guide are comprised of materials that have essentially the same index of refraction.

7. The laser instrument of claim 1, wherein the application cap and the light guide are comprised of a quartz glass material.

8. A method for vaporization of a biological tissue, comprising:
   providing an optical waveguide comprising a light guide portion having a distal end and configured to emit a light;
   providing an application cap coupled to the optical waveguide and configured to transmit the light, comprising:
      an axial cap part into which the light guide is at least partially inserted, that has a first longitudinal axis; and
      a bent cap part that angularly extends from the axial cap part and has a second longitudinal axis that extends at a first angle relative to the first longitudinal axis, wherein the transition from an exterior surface of the axial cap part to an exterior surface of the bent cap part defines a maximum exterior angle and a minimum exterior angle,
   wherein the axial cap part extends beyond the distal end of the light guide portion for a distance that causes the light emitted from the distal end to be transmitted through the application cap within a first radial limit defined by a first linear path from the distal end through the vertex of the maximum exterior angle, and the first angle has an angular size that causes the light emitted from the distal end to be transmitted through the application cap within a second radial limit defined by a second linear path from the distal end through a distal edge of the exterior surface of the bent cap part that defines the minimum exterior angle; and transmitting a light to vaporize the biological tissue from the optical waveguide through the application cap and upon the biological tissue.

9. The method of claim 8, further comprising roughening the texture of an exterior surface of the application cap defined between the first radial limit and the second radial limit; and contacting the biological tissue with the roughened exterior surface to abrade and collect the biological tissue thereupon.

10. The method of claim 8, further comprising:

inserting the axial cap part of the application cap at least partially into an endoscope;

extending the application cap from the endoscope to move the application cap toward the biological tissue; and retracting the application cap within the endoscope to move the application cap away from the biological tissue.

* * * * *

UNITED STATES PATENT AND TRADEMARK OFFICE
CERTIFICATE OF CORRECTION

| | | |
|---|---|---|
| PATENT NO. | : 6,699,239 B1 | Page 1 of 1 |
| APPLICATION NO. | : 09/700948 | |
| DATED | : March 2, 2004 | |
| INVENTOR(S) | : Stiller et al. | |

It is certified that error appears in the above-identified patent and that said Letters Patent is hereby corrected as shown below:

Column 2, line 17: "invention;" should read --invention--

Column 3, line 33: "manners" should read --manner--

Column 3, line 44: "_ "a"_" should read --"a"--

Column 3, line 45: "_ "α"_" should read --"α"--

Column 3, lines 48 to 49: "_ "Ra"_ of the ray bundle emerges at a maximum exterior angle" should read -- "Ra" of the ray bundle emerges--

Column 3, line 51: " _"Ri"_" should read --"Ri"--

Column 3, lines 52 to 53: "10 which form a minimum exterior angle on this side," should read --10,--

Column 3, line 56: "_"P"_" should read --"β"--

Signed and Sealed this

Twenty-second Day of August, 2006

JON W. DUDAS
*Director of the United States Patent and Trademark Office*